United States Patent [19]

Drent

[11] Patent Number: 4,868,345
[45] Date of Patent: Sep. 19, 1989

[54] PROCESS FOR HYDROGENATION OF ESTERS INTO ALCOHOLS

[75] Inventor: Eit Drent, Amsterdam, Netherlands

[73] Assignee: Shell Oil Company, Houston, Tex.

[21] Appl. No.: 238,384

[22] Filed: Aug. 31, 1988

[30] Foreign Application Priority Data

Sep. 15, 1987 [GB] United Kingdom ................. 8721699

[51] Int. Cl.$^4$ ..................... C07C 29/136; C07C 31/04; C07C 31/10; C07C 31/20
[52] U.S. Cl. ..................................... 568/885; 568/814; 568/864
[58] Field of Search ......................... 568/885, 814, 864

[56] References Cited

U.S. PATENT DOCUMENTS

| | | | |
|---|---|---|---|
| 4,232,170 | 11/1980 | Grey et al. | 568/885 |
| 4,346,240 | 8/1982 | Grey et al. | 568/814 |
| 4,614,749 | 9/1986 | Sapienza et al. | 518/700 |
| 4,619,946 | 10/1986 | Sapienza et al. | 518/700 |
| 4,623,634 | 11/1986 | Sapienza et al. | 502/113 |

OTHER PUBLICATIONS

Gallois et al, "Activation of Reducing Agents", J. Org. Chem., 45, 1946–1950 (1980).

Primary Examiner—J. E. Evans

[57] ABSTRACT

A process for the hydrogenation of esters into alcohols which comprises converting esters of the formula

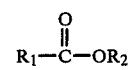

wherein $R_1$ is hydrogen or a hydrocarbyl group and preferably an alkyl group containing 1–20 carbon atoms or an aryl alkyl group containing 1–6 carbon atoms in the alkyl residue, the aryl being preferably phenyl, and $R_2$ is a hydrocarbyl group as specified hereinbefore for $R_1$, in the presence of hydrogen and carbon monoxide and a catalyst system, obtainable by combining the following components (a) a hydride of an alkali metal and/or a hydride of an alkaline earth metal,
(b) an alcohol or an alkali metal and/or alkaline earth metal alcoholate thereof, and
(c) a compound containing a cation of an element of Group VIII of the Periodic Table of the Elements, and allowing these components to react.

23 Claims, No Drawings

PROCESS FOR HYDROGENATION OF ESTERS INTO ALCOHOLS

FIELD OF THE INVENTION

The invention relates to a process for the hydrogenation of esters and more particularly to a process for the hydrogenation of esters into alcohols in the presence of hydrogen and carbon monoxide and in the presence of a catalyst system.

BACKGROUND OF THE INVENTION

Such processes for the hydrogenation of esters are in general known from a great variety of literature and using a large number of diverging types of catalysts. However, all these catalytic hydrogenation processes have in common that they operate inseparable from the application of high pressures and high temperatures and moreover require the use of pure hydrogen as reducing agent.

It will be appreciated that such relative extreme reaction conditions put heavier demands to construction and materials for the equipment to be used for these processes, which means a significant operational cost increasing factor.

Therefore, there is still a need for an improved process of the hydrogenation of esters into alcohols, which may be carried out under economically attractive operational conditions and which should not inevitably require pure hydrogen gas but should be carried out in the presence of hydrogen containing gases such as synthesis gas ($H_2:CO=2:1$) or other commercially available hydrogen containing gas mixtures optionally containing inert gas components, such as helium or nitrogen.

As a result of extensive research and experimentation such an improved process aimed at, was surprisingly found.

SUMMARY OF THE INVENTION

The present invention is a process for the hydrogenation of esters of the formula

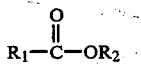

wherein $R_1$ is hydrogen or a hydrocarbyl group and preferably an alkyl group containing 1–20 carbon atoms or an aryl alkyl group containing 1–6 carbon atoms in the alkyl residue, the aryl being preferably phenyl, and wherein $R_2$ is a hydrocarbyl group as specified herein before for $R_1$, in the presence of hydrogen and carbon monoxide and a catalyst system, obtainable by combining the following components (a) a hydride of an alkali metal and/or a hydride of an alkaline earth metal,
(b) an alcohol or an alkali metal and/or alkaline earth metal alcoholate thereof, and
(c) a compound containing a cation of an element of Group VIII of the Periodic Table of the Elements, and allowing these components to react.

DETAILED DESCRIPTION OF THE INVENTION

Component (a) may be a hydride of lithium, sodium, potassium, rubidium, cesium, calcium, strontium, barium or magnesium. Preference is given to sodium hydride. The hydride may be added as such, but it has been found that the hydride may advantageously be added as a suspension in an inert diluent, for example a mineral oil, such as a heavy hydrocarbon oil, preferably a so-called white paraffin oil.

The alcohol of component (b) may be cycloaliphatic or aliphatic, but is preferably aliphatic. Preference is given to alkanols, in particular to those having in the range of from 1 to 20 carbon atoms per molecule. Among the latter alkanols those having in the range of from 4 to 20 carbon atoms per molecule are preferred. Tertiary alcohols are more preferred. Examples of suitable alkanols are tert-butyl alcohol, tert-pentyl alcohol, hexanol, heptanol and alkanols with from 8 to 20 carbon atoms per molecule. Tert-butyl alcohol and tert-pentyl alcohol are particularly preferred.

Dihydric alcohols may also be used, for example ethylene glycol, propylene glycol, 1,3-dihydroxypropane, 1,2-butanediol, 1,3-butanediol, 1,4-butanediol, 2,3-butanediol or 1,2-pentanediol. Component (b) may also be glycerol.

Component (b) may be a mixture of alcohols, for example of tert-butyl alcohol and ethylene glycol or of tert-phenyl alcohol and 1,4-butanediol.

The alcoholate to be used is preferably a sodium alcoholate or a potassium alcoholate. Among the alcoholates preference is given to alkoxides, particularly to those having from 1 to 20 carbon atoms per molecule, such as sodium methoxide, sodium ethoxide, sodium propoxide, sodium butoxide, sodium isobutoxide, sodium tert-pentoxide and potassium 2-methyldodec-2-oxide.

The elements of Group VIII of the Periodic Table of the Elements that may be used in the salt of component (a) are iron, cobalt, nickel, ruthenium, rhodium, palladium, osmium, iridium and platinum. Preference is given to nickel.

The anion of the salt in component (c) may be derived from a great variety of acids. It is preferred that the salt in component (c) is a salt of a carboxylic acid or sulphonic acids. Among these acids preference is given to alkanoic acids having 1-10 carbon atoms in the chain or to paratoluene sulphonic acid. More preference is given to formic acid, acetic acid and oxalic acid. Component (c) is most preferably nickel formate, nickel acetate, nickel oxalate or nickel tosylate.

Examples of carboxylic acids from which component (c) also may be derived are dicarboxylic acids such as malonic acid, dimethylmalonic acid, succinic acid, glutaric acid, adipic acid, pimelic acid, suberic acid, azelaic acid, phthalic acid, isophthalic acid and terephthalic acid. The carboxylic acids from which component (c) may be derived may contain substituents, for example alkoxy groups, particularly those having not more than five carbon atoms, hydroxy groups, cyano groups and fluorine, chlorine, bromine and iodine atoms. Examples of such carboxylic acids are glycolic acid, 2-hydroxypropionic acid, 3-hydroxypropionic acid, glyceric acid, tartronic acid, malic acid, tartaric acid, tropic acid, benzilic acid, salicylic acid, anisic acid, gallic acid, 3,5-dichlorobenzoic acid, 3,5-dibromobenzoic acid, cyanoacetic acid, monofluoroacetic acid, difluoroacetic acid, trifluoroacetic acid and trichloroacetic acid.

Other examples of suitable acids from which component (c) may be derived are propanoic acid, butanoic acid, 2-methylpropanoic acid, pentanoic acid, 3-methylbutanoic acid, 2,2-dimethylpropanoic acid, hexanoic acid, heptanoic acid and octanoic acid, hydrochloric acid, sulphuric acid, nitric acid and phosphoric acid.

A mixture of the salts in question may be used in component (c), for example of a formate and an oxalate, of a formate and an acetate, of acetate and an oxalate.

The salts in component (c) may contain crystal water, but are preferably free therefrom.

The activation of the catalyst system, which has appeared to provide the most attractive results, may be reached by keeping the mixed components under an atmosphere of nitrogen or any other suitable inert gas during 0.3 to 1 hour at a temperature in the range of from 20°–60° C. and more preferably 35°–50° C.

The process according to the present invention may be carried out at a temperature and a pressure which are not critical and may vary within wide ranges. Preferably, a temperature in the range of from 30° C. to 150° C. and a pressure in the range of from 5 to 100 bar are used.

The process according to the present invention may be carried out with an organic diluent in which the catalytic system is dissolved or suspended. Suitably, a weight ratio of organic diluent to component (c) in the range of from 0.1 to 5000 is used, but this weight ratio may be lower than 0.1 or higher than 5000.

Any inert diluent may in principle be used. Examples of suitable diluents are ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzene; halogenated alkanes, such as dichloromethane and carbontetrachloride; alkanes, such as hexane, heptane, octane, 2,2,3-trimethylpentane and kerosene fractions; cycloalkanes, such as cyclohexane and methylcyclohexane; sulphones, such as diisopropyl sulphone, tetrahydrothiophene 1,1-dioxide (also referred to as "sulfolane"), 2-methyl-4-butylsulfolane and 3-methylsulfolane. Mixtures of two or more solvents may be used. Very good results have been obtained with ethers and the use of diglyme is most preferred.

The process according to the present invention is preferably carried out using a molar ratio of the starting ester to component (c) in the range of from 0.5:1 to 100:1 and, more preferably, from 1:1 to 50:1, but the use of molar ratios below 0.5 and above 100 is not excluded. The process may be carried out using a molar ratio of component (b) to component (c) which is not critical and may vary within wide ranges, preferably in the range of from 0.1:1 to 100:1.

The carbon monoxide and hydrogen may be used as pure gases or diluted with an inert gas such as a noble gas or nitrogen. The process according to the present invention may be carried out using a molar ratio carbon monoxide to hydrogen in the gaseous mixture which is not critical and may vary within wide ranges, suitably in the range of from 1:0.2 to 1:20. The carbon monoxide and hydrogen may be obtained by partial oxidation of hydrocarbons, for example of natural gas.

It is true, that a representative of the catalyst systems to be used according to the present invention is known per se from e.g. U.S. Pat. No. 4,614,749 issued Sept. 30, 1986. However, in the latter the use of such catalyst systems for the production of methanol from carbon monoxide and hydrogen is disclosed and it will be appreciated that a person skilled in the art cannot find any teaching therein in order to come to the present process.

The same may be concluded with reference to the disclosure in J. Org. Chem. 1980, 45, 1946–1950 of similar catalyst systems for the selective hydrogenation of carbon-carbon double bonds in the presence of oxo groups and hydrogenations of carbonyl groups.

It will be appreciated that the attractive results obtained according to the process of the invention using mixtures of $H_2$ and CO are very surprising.

According to a specific embodiment of the process of the present invention methylformate, methylacetate or methyl proprionate is hydrogenated into methanol and/or ethanol and/or n-propanol and methanol at 120° C. and a total pressure of 30–50 bar, leading to more than 90% conversion in 5 hours.

In about the same way methyl succinate may be hydrogenated into butanediol and methanol.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The following examples further illustrate the invention, without however restricting the scope thereof to these particular embodiments.

All experiments were carried out in a 300 ml magnetically stirred Hastelloy C (Hastelloy is a trade name) autoclave.

The reaction mixtures obtained were analyzed by means of gas-liquid chromatography.

EXAMPLE 1

The autoclave is initially charged with 50 ml diglyme, 10 mmol nickel(II)formate, 60 mmol sodium hydride, 20 mmol tert-amylalcohol. The catalyst system was activated during 0.5 hour at 45° C. under nitrogen.

Thereafter 30 mmol tert-amylalcohol in 50 ml diglyme and 10 ml methylpropionate were added. Carbon monoxide is added to a partial pressure of 5 bar, while hydrogen is added to a partial pressure of 30 bar at ambient temperature.

The reaction mixture was then heated up to 80° C. and kept at this temperature during two hours, whereafter the reaction mixture was kept for three hours at 120° C. When the total reaction pressure had decreased until about 30 bar hydrogen gas was added until a total operational pressure of about 60 bar was reached.

After termination of the reaction, the mixture was allowed to cool to room temperature and analyzed. 5.1 g Propanol and 3.5 g methanol were found.

COMPARATIVE EXAMPLE A

In about the same way as described under Example 1 an experiment was carried out, with the difference that no carbon monoxide was included. No real hydrogenation reaction could be observed by means of pressure drop. In the reaction mixture only some of methanol and traces of propanol could be detected.

EXAMPLE 2

In about the same way as described under Example 1, an experiment was carried out, with the difference that the autoclave was charged with 8 ml dimethylsuccinate (instead of 10 ml methyl propionate). Carbon monoxide was added to a partial pressure of 5 bar, and hydrogen was added to a partial pressure of 54 bar (at ambient temperature). The reaction mixture was heated to 80° C. and kept at this temperature for two hours, whereafter the temperature was kept at 120° C. for five hours. After termination of the reaction, 4 g methanol and 2.5 g 1,4-butanediol was detected.

EXAMPLE 3

In the same way as described under Example 1, an experiment was carried out, with the difference that 10 mmol nickel(II)tosylate and 20 ml methyl propionate was included in the starting reaction mixture. The reaction mixture was kept at 80° C. for two hours and at 100° C. for 3 hours.

After about 45 min from the start of the reaction hydrogen was added to a partial pressure of 40 bar, while after 3 hours 20 bar hydrogen was added. After termination of the reaction 7.4 g propanol and 4.8 g methanol were obtained.

EXAMPLE 4

In about the same way as described under Example 1, an experiment was carried out with the difference that after activation at 45° C. 20 ml tert-amylalcohol and 20 ml methyl propionate are added.

The autoclave is filled with carbon monoxide up to a partial pressure of 5 bar and with hydrogen up to 30 bar. The temperature of the reaction mixture was kept at 80° C. for two hours and at 100° C. for three hours.

After about 0.5 hour from the start of the reaction hydrogen was added to a pressure increase of 30 bar and after 1.5 hour hydrogen was added to a pressure increase of 20 bar. After termination of the reaction 5.2 g methanol and 7.9 g propanol were present in the reaction mixture.

EXAMPLE 5

In about the same way as described in Example 4, an experiment was carried out with the difference that after activation in addition to the before mentioned ingredients 5 ml pyridine were added. The reaction temperature was kept at 100° C. for 5 hours. Additional amounts of hydrogen were added after 5 minutes, 15 minutes and one hour respectively from the start of the reaction (each time pressure increase 10 bar). Addition of carbon monoxide took place after 1.25 hour up to a pressure increase of 5 bar. After termination of the reaction, 6.5 g propanol and 4.2 g methanol were present in the reaction mixture.

I claim:

1. A process for the hydrogenation of esters into alcohols which comprises converting esters of the formula

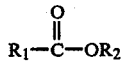

wherein $R_1$ is hydrogen or a hydrocarbyl group selected from the group consisting of an alkyl group containing 1-20 carbon atoms or an aryl alkyl group containing 1-6 carbon atoms in the alkyl residue, and $R_2$ is a hydrocarbyl group as specified hereinbefore for $R_1$, in the presence of hydrogen and carbon monoxide and a catalyst system, obtainable by combining the following components (a) a hydride of an alkali metal and/or a hydride of an alkaline earth metal, (b) an alcohol or an alkali metal and/or alkaline earth metal alcoholate thereof, and (c) a compound containing a cation of an element of Group VIII of the Periodic Table of the Elements, and allowing these components to react.

2. The process as claimed in claim 1, characterized in that component (a) is selected from a hydride of lithium, sodium, potassium, rubidium, cesium, calcium, strontium, barium or magnesium.

3. The process as claimed in claim 2, characterized in that sodium hydride is used.

4. A process as claimed in any one of claims 1 to 3, characterized in that the hydride is added in the form of a suspension in an inert diluent.

5. The process as claimed in claim 1 characterized in that as component (b) an alkanol having 4 to 20 carbon atoms, is used.

6. The process as claimed in claim 5, characterized in that tert.-butylalcohol or tert-pentylalcohol is used.

7. The process as claimed in claim 1, characterized in that component (b) consists of a sodium alcoholate or a potassium alcoholate.

8. The process as claimed in claim 7, characterized in that sodium methoxide, sodium ethoxide, sodium propoxide, sodium butoxide, sodium isobutoxide, sodium tert-pentoxide or potassium 2-methyldodec-2-oxide is used.

9. The process as claimed in claim 1, characterized in that a nickel salt is used.

10. The process as claimed in claim 9, characterized in that nickel formate, nickel acetate, nickel oxalate or nickel tosylate is used.

11. The process as claimed in claim 1, characterized in that the catalyst system of the mixed catalyst components is activated by treating the mixture with nitrogen during 0.3 to 1 hour and at a temperature in the range of from 20°-60° C.

12. The process as claimed in claim 1, characterized in that the reaction is carried out at a temperature in the range of from 30° C. to 150° C.

13. The process as claimed in claim 1, characterized in that the reaction is carried out at a pressure in the range of from 5 to 100 bar.

14. The process as claimed in claim 1, characterized in that the reaction is carried out in an organic diluent.

15. The process as claimed in claim 1, characterized in that a weight ratio of organic diluent to component (c) is in the range of from 0.1 to 5000.

16. The process as claimed in claim 1, characterized in that a molar ratio of the starting ester to component (c) is in the range of from 0.5:1 to 100:1.

17. The process as claimed in claim 16, characterized in that the molar ratio is in the range of from 1:1 to 50:1.

18. The process as claimed in claim 1, characterized in that a molar ratio of component (b) to component (c) in the range of from 0.1:1 to 100:1 is used.

19. The process as claimed in claim 1, characterized in that an ether is used as diluent.

20. The process as claimed in claim 19, characterized in that diglyme is used as diluent.

21. The process as claimed in claim 1, characterized in that a molar ratio of carbon monoxide to hydrogen in the range of from 1:0.2 to 1:20 is used.

22. The process as claimed in claim 1, characterized in that the aryl group is phenyl.

23. The process as claimed in claim 1, characterized in that methylformate, methylacetate or methylpropionate is hydrogenated.

* * * * *